United States Patent [19]

Idemoto et al.

[11] Patent Number: 5,180,363
[45] Date of Patent: Jan. 19, 1993

[54] OPERATION DEVICE

[75] Inventors: Morito Idemoto; Naohiko Inoue; Yasuo Noguchi, all of Yokohama, Japan

[73] Assignee: Sumitomo Bakelite Company Company Limited, Tokyo, Japan

[21] Appl. No.: 813,053

[22] Filed: Dec. 23, 1991

Related U.S. Application Data

[63] Continuation of Ser. No. 422,270, Oct. 16, 1989, abandoned.

[30] Foreign Application Priority Data

Apr. 27, 1989 [JP] Japan .................... 1-106044

[51] Int. Cl.⁵ .................... A61B 17/32; H01L 41/08
[52] U.S. Cl. .................... 202/32; 128/24 AA;
606/39; 606/45; 606/170; 606/171; 310/316;
310/325
[58] Field of Search .............. 128/24 AA, 41; 604/22,
604/27, 44; 73/1 DV; 606/37-39, 45, 169, 170,
171, 172; 310/316, 317, 318, 319, 325

[56] References Cited

U.S. PATENT DOCUMENTS

| | | |
|---|---|---|
| 4,056,761 | 11/1977 | Jacoby et al. . |
| 4,108,182 | 8/1978 | Hartman et al. ............... 606/171 |
| 4,188,952 | 2/1980 | Loschilov et al. .............. 128/24 AA |
| 4,271,371 | 6/1981 | Furuichi et al. ............... 310/316 |
| 4,634,419 | 1/1987 | Kreizman et al. .............. 128/24 AA |
| 4,754,186 | 6/1988 | Choperena et al. ............. 310/316 |
| 4,816,743 | 3/1989 | Harms et al. .................. 310/316 |
| 4,838,853 | 6/1989 | Parisi .......................... 128/24 AA |
| 4,893,045 | 1/1990 | Honda ......................... 310/325 |
| 4,922,902 | 5/1990 | Wuchinich et al. .............. 607/22 |
| 4,965,532 | 10/1990 | Sakurai ........................ 310/316 |

FOREIGN PATENT DOCUMENTS

| | | |
|---|---|---|
| 0229003 | 11/1985 | European Pat. Off. . |
| 0272657 | 12/1986 | European Pat. Off. . |
| 6110194 | 1/1986 | Japan . |
| 2212305 | 12/1987 | United Kingdom . |

*Primary Examiner*—Lee S. Cohen
*Assistant Examiner*—K. M. Pfaffle
*Attorney, Agent, or Firm*—Browdy and Neimark

[57] ABSTRACT

A surgical operation device comprising an ultrasonic piezoelectric transducer for generating ultrasonic vibrations, an oscillation feedback type oscillator for supplying high-frequency power to the ultrasonic transducer, a vibration transmitter connected to the ultrasonic transducer for transmitting and amplifying mechanical vibrations at an ultrasonic frequency, a suction unit and an irrigator. The ultrasonic transducer includes a bolted Langevin type transducer. The feedback circuit of the oscillation feedback type oscillator includes an oscillation voltage detector, a phase comparator, a low pass filter, a differential amplifier, and a voltage controlled oscillator. Thus, the mechanical resonant frequency can be traced in a wide range of fluctuations of a load on the vibration transmitter during vibration and vibrations can start an appropriate mechanical resonate frequency irrespective of the load status of the vibration transmitter at the start-up.

16 Claims, 13 Drawing Sheets

F I G. 14A
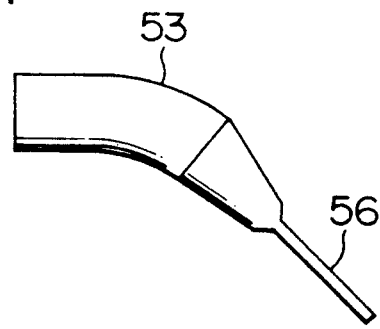
F I G. 14B
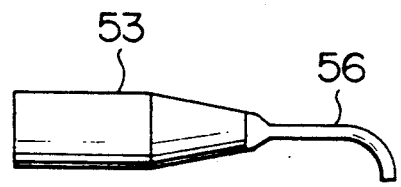
F I G. 15A
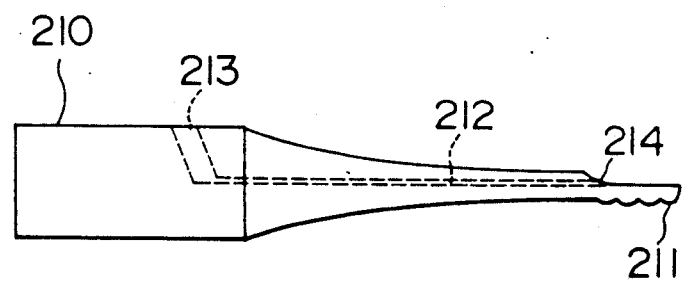
F I G. 15B
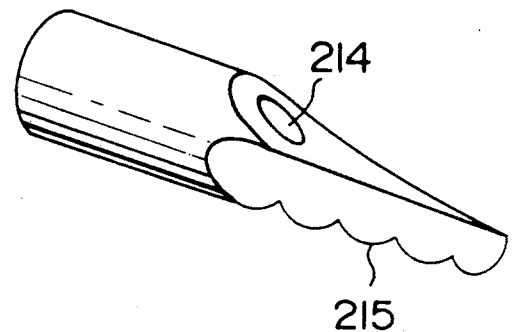

OPERATION DEVICE

This application is a continuation of application Ser. No. 07/422,270, filed Oct. 16, 1989, now abandoned.

BACKGROUND OF THE INVENTION

The present invention relates to surgical operation devices for crushing, severing and/or cutting the organization of an organism using ultrasonic vibrations.

Known operation devices which use ultrasonic waves are devices for crushing and/or cutting the organization of an organism in the fields of orthopedic and general surgical operations, devices for operating cataract in the field of ophthalmology and ultrasonic operation devices for scaling the teeth in the field of dental surgery. Any of these devices includes an ultrasonic oscillator, an ultrasonic piezoelectric transducer, an ultrasonic wave transmitter which constitute a single resonant system which oscillates ultrasonically at a particular resonant frequency. Usually, the operation section of the ultrasonic vibration transmitter contacts an organism, so that a mechanical load acts on the operation section. The load on the oscillator fluctuates in accordance with contact state. Therefore, the oscillating frequency and mechanical resonant frequency of the oscillator differ from each other and it is difficult to maintain the amplitude and vibrating speed of the operation section at constant appropriate conditions.

In order to cope with such fluctuations of the load, an oscillation feedback oscillation is known in which if an ultrasonic vibration transmitter is connected and driven with a constant current or voltage, in order to cope with fluctuations of the load, the mechanical Q of the resonant system is high, so that the amplitude and vibrating speed of the operation section is maximum at the mechanical resonant frequency. This amplitude and vibrating speed are extracted by using an appropriate device or method proportional to the amplitude and fed back to the input terminal of an amplifier to maintain oscillation at all times even if the mechanical resonant frequency fluctuates. An oscillator is used in which a pickup device is attached to a piezoelectric transducer to obtain a voltage in proportion to vibration and to feed back the voltage to the input terminal of the amplifier. The attachment of the pickup device to the transducer renders structurally complicated and a large-sized handpiece including the transducer. This is against miniaturization and lightening of the handpiece as an operation device for medical treatment manipulated by the operator.

There is proposed a method in which a voltage in proportion to the vibration is extracted by an electrical circuit. In this case, an oscillator is used in which an oscillating voltage detector is used as a feedback circuit (see FIGS. 20, 21). A voltage in proportion to the vibration is extracted as an output voltage 105 to a transducer 104 from a matching circuit 102 by an oscillating voltage detecting motional bridge 107 of a feedback circuit 103 and fed back to the input terminal 106 of an amplifier 101, as shown in FIGS. 19 and 20. If a load is applied to the operation section before oscillation starts, the mechanical resonant frequency of the resonant system including the piezoelectric transducer and the ultrasonic vibration transmitter greatly tends to be a spurious frequency at the start-up. In addition, under such condition, the oscillation is fixed by the feedback circuit 103 in the spurious mode, so that it is difficult to restore the predetermined mechanical resonant frequency. If the difference between the mechanical resonant frequency and the oscillating frequency is out of the narrow resonant frequency of the matching circuit 102 of the oscillator or of filters of the amplifier 101 by fluctuations of the load on the vibrating operation section, feedback would not be effected and oscillation would stop undesirably.

An ultrasonic oscillator including a feedback circuit using a PLL (Phase-Locked Loop) (Japanese Patent Publication JP-A-61-10194) uses the feature of the PLL to cause a piezoelectric transducer to sweep frequencies in a predetermined range to lock the oscillating frequency to the mechanical resonant frequency. If the resonant system is driven which includes an ultrasonic vibration transmitter connected to the piezoelectric transducer and has a greatly changing load thereon, the direct supply of a feedback signal from the transducer to a phase comparator of the PLL makes it impossible to discriminate between the spurious frequency and the optimum resonant frequency generated when the amplitude and vibrating speed of the operation section are maximum and the vibration may be likely to be fixed in the spurious mode. Thus, especially, it is difficult to vibrate an ultrasonic vibration transmitter in large load fluctuation and especially used for severing and/or cutting a hard organization.

While a magnetostrictive transducer is often used as a power transducer, the efficiency of its electro-mechanical conversion is low, radiation loss from the transducer is high and the transducer would be deteriorated unless it is cooled by water, for example. Thus, a power electrostrictive bolted Langevin transducer higher in electro-mechanical conversion efficiency than the magnetostrictive transducer has been invented. The Langevin transducer is low in heat generation compared to the magnetostrictive transducer, so that a special-purpose cooling mechanism is not needed. FIG. 21 schematically illustrates a Langevin transducer in which one of metal blocks 108, 109 has a bolt portion and the other has a nut portion. The bolt portion has ring-like polarized electrostrictive transducers 112, 113 and electrodes 114, 115, 116 fitted alternately thereon and tightened by the other (nut) of the blocks 108 and 109. High-frequency power is applied across the electrode plates 114, 115 and 116 from the oscillator to cause ultrasonic vibrations. At this time, the metal block 108 contacting the ultrasonic vibration transmitter 117 which directly contacts the organization of an organism have to be used grounded. According to classification of dangerous degree of electrical shocks this system is a B-type medical device, so that it cannot be applied directly to human hearts.

One example of the structure of a conventional handpiece using an ultrasonic vibration transmitter to crush, suck and eliminate a soft organization will be described somewhat in detail with reference to FIG. 22. An ultrasonic vibration transmitter 119 is connected to an ultrasonic vibration source 118 as by screws. The transmitter 119 includes a constant cross-sectional area (for example, cylindrical) portion 126 of a ¼ wavelength, a tapered portion and a minimum-diameter pipe-like operation section 122 for generation of ultrasonic vibrations. The transmitter 119 has a longitudinally extending internal path 120 through which celluar fragments crushed and emulsified by the operation section 122 and an irrigation solution supplied to a position where operation is effected are sucked and eliminated to the outside.

The distribution of stress on the transmitter 119 is expressed by a stress line 123 in FIG. 22(b). The internal stress produced when ultrasonic vibrations occur is zero at the end of the ultrasonic vibration source 118 and the operation section 122. The maximum point on the stress line 123 appears at the minimum cross section area 121 of the tapering portion. FIG. 22(c) illustrates the amplitude corresponding to the stress. The amplitude amplification rate is directly proportional to the ratio of cross section area $S_1$ of the cylindrical portion 126 to cross section area $S_2$ of the operation section 122, $S_1/S_2$. Similarly, the internal stress is also proportional directly to the cross section area ratio between portion 126 and 121.

A large amplitude is required to crush the organization of an organism, especially, calcification so that it is necessary to increase the cross section area ratio in the ultrasonic vibration transmitter 119. As a result, a metal fatigue and hence breakage due to ultrasonic vibration may occur at the minimum tapering end 121 to which the maximum stress applies. Thus, if a high-amplitude handpiece is designed which prevents a breakage at the minimum cross section area 121, it would be greatly deformed and not suitable for practical use.

If a position where operation is effected is deep in a living body and the operating field is very narrow, very difficult operation is forced to thereby take a long time, which is an obstacle to an appropriate and accurate operation.

When a hard organization is conventionally severed and cut, Kerrison foceps, chisels, raspatories, surgical burs, etc., are used. Operation devices such as Kerrison foceps and line saws are low in operation efficiency, take much time, take much energy from the operator, and require fine operation and high techniques. An air-driven surgical bur rotates a drill to sever and cut the affected portion of a living body, so that small vibrations are transmitted to the hand of the operator from an area where the bur contacts the hard organization during operation, and hence a fine operation is difficult. In addition, the activeness of the organization of an organism would be lost by frictional heat due to rotation of the drill. Furthermore, the rotational movement of the drill would damage the organization of blood vessel and nerves in a hard organization only by touching the organization.

SUMMARY OF THE INVENTION

In order to solve such problems with the conventional surgical operation devices, the present invention provides a surgical operation device which includes an ultrasonic oscillator capable of widely tracing the mechanical resonant frequency in accordance with load fluctuation and starting with an appropriate frequency, a bolted CF-type Langevin transducer of a reduced leakage current, an ultrasonic vibration transmitter of high fatigue strength and for a soft organization, and an ultrasonic vibration transmitter for severing and/or cutting a hard organization efficiently.

The present invention provides a surgery operation device comprising:

an ultrasonic piezoelectric transducer for generating ultrasonic vibrations;

an oscillation feedback type oscillator for supplying high-frequency power to the transducer;

a vibration transmitter connected to the resonator for transmitting and amplifying a mechanical vibration at an ultrasonic frequency;

a sucking unit; and an irrigator;

wherein the piezoelectric transducer includes a bolted Langevin type transducer; and wherein the feedback circuit of the oscillation feedback oscillator includes an oscillation voltage detector, a phase comparator, a low pass filter, a differential amplifier, and a voltage controlled oscillator.

BRIEF DESCRIPTION OF THE DRAWINGS

FIGS. 6-14B illustrate the shape, vibration and distribution of stress of an ultrasonic vibration transmitter as one embodiment of the present invention;

FIGS. 15A-17B illustrate one embodiment of a severing/cutting ultrasonic vibration transmitter;

DESCRIPTION OF THE PREFERRED EMBODIMENTS

Figure 1:
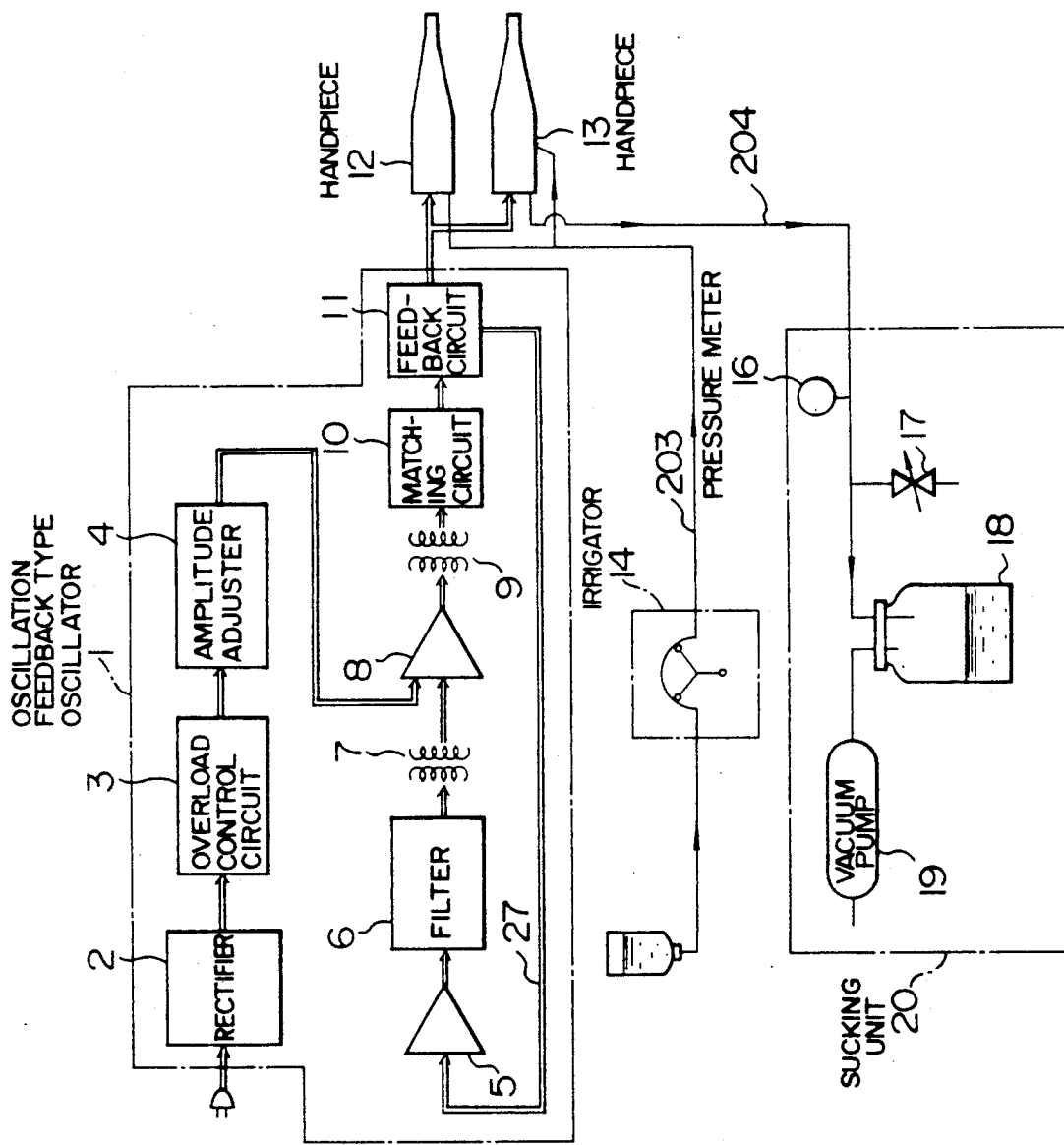
FIG. 1 is a block diagram of one embodiment of a surgical operation device according to the present invention.

The present invention will now be described in detail with reference to the drawings. FIG. 1 is a block diagram of a surgical operation device as one embodiment of the present invention. The device has an ultrasonic function, an irrigation function, and a sucking function. The irrigation function is to cause an irrigator 14 to supply a liquid which does not damage the tissues, for example, physiological saline solution, to operation sections at the end of handpiece 12 or 13 via a tube 203 to cool the operation sections and their ambient organism organizations using the liquid, and to generate a cavitation due to the ultrasonic vibrations of the operation sections to crush tissues. The sucking function is to cause a sucking unit 20 to suck and eliminate fragments of tissues crushed by the operation sections at the end of the handpiece 12 or 13 out of the living body. A negative pressure (vacuum) generated by a vacuum pump 19 is adjusted by a pressure adjuster valve 17 and a pressure meter 16 to an appropriate sucking pressure so that the fragments of tissues are stored in a bottle 18 via a tube 204. The ultrasonic function is to cause an oscillation feedback type oscillator 1 to generate an electrical energy of ultrasonic frequency (18-38 KHz), to apply the electric energy to bolted Langevin type resonators in the handpiece 12 or 13 to generate mechanical ultrasonic vibrations, and to cause the vibration transmitters connected to the transducers to increase the vibration amplitude and speed to thereby crush, sever and cut the affected portion of a living body using ultrasonic vibrations of the operation sections.

The oscillation feedback type oscillator 1 according to the present invention has a circuit to maintain an ultrasonic vibration of a predetermined resonant frequency even if the load on the operation section fluctuates greatly, namely, even if a hard organization is severed/cut. In the oscillator 1, a predetermined AC source current is rectified by a rectifier 2 to provide direct current sources for driving circuit elements in the oscillator 1. A current flows from the rectifier 2 to an overload control circuit 3, and an amplitude adjuster 4. The overload control circuit 3 interrupts a current using a device such as a thyristor when a current exceeding a maximum predetermined value flows through the unit 3. The threshold current is preferably 1.5-3A although not limited. The amplitudes of the ultrasonic vibrations generated by the handpiece 12 or 13 are adjusted by varying the output voltage of the amplitude adjuster 4.

In oscillation, a signal of a reference frequency output from the feedback circuit 11, namely, a signal of the resonant frequency of the handpieces is inputted to and amplified by the amplifier 5 and the resulting signal is delivered through a filter 6 and a transformer 7 to an amplifier 8. The filter 6 includes a bandpass filter centered at the resonant frequency and preferably passes therethrough a band of a resonant frequency ±1-3 KHz although not especially limited. The signal voltage is enhanced by the transformer 7 and the resulting voltage is applied to the amplifier 8 which amplifies the signal current of the resonant frequency from the transformer 7 in accordance with the current from the amplitude adjuster 4. The resulting signal is enhanced by a transformer 9 and is delivered to a matching circuit 10 which performs impedance matching between the handpiece 12 or 13 and the oscillator 1. The output from the matching circuit 10 is delivered to the feedback circuit 11. The amplifier 8 is preferably a SEPP circuit or a B-class push-pull circuit although not especially limited.

Figure 2:
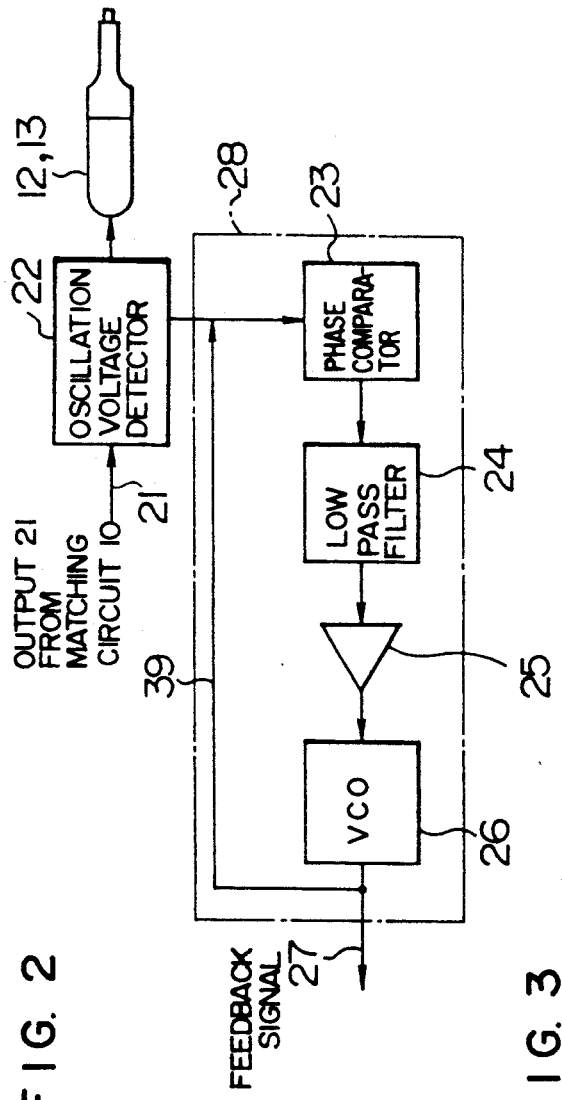
FIGS. 2-4 are a block diagram and a circuit diagram of an oscillation feedback type oscillator.
Figure 3:
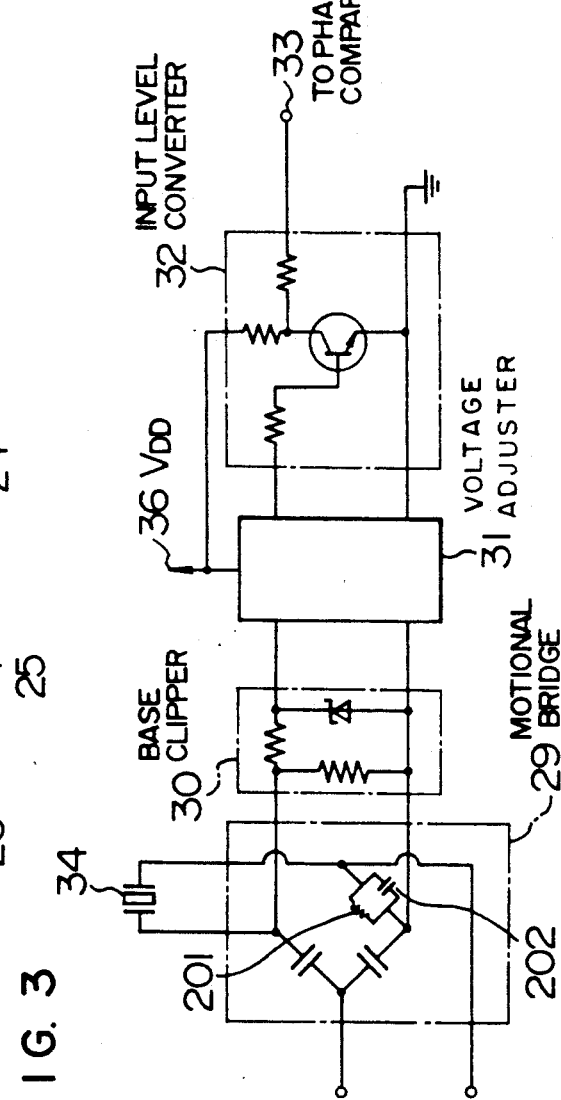
Figure 4:
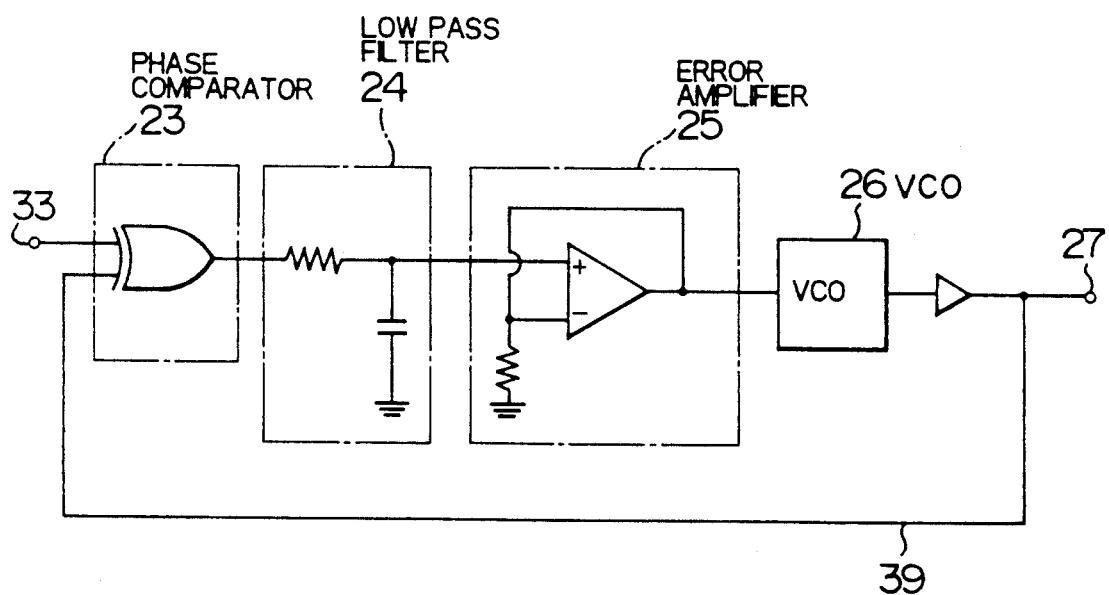

FIG. 2 illustrates the details of the feedback circuit 11. The output 21 from the matching circuit 10 is supplied to the handpiece 12 or 13 via an oscillation voltage detector 22 which includes a motional bridge 29, a base clipper 30, a voltage adjuster 31 and an input level converter 32, as shown in FIG. 3. The output 21 from the matching circuit 10 is applied across two terminals on a diagonal line of the motional bridge 29 to drive a bolted Langevin type transducer 34 included in the handpiece 12 or 13 connected in a branch of the bridge. A resistor 201 cooperating with a capacitor 202 to form a parallel circuit of the motional bridge 29 may be removed if a plurality of capacitors are connected in series to adjust a breakdown voltage. The output from other two terminals of the motional bridge 29 through a base clipper 30, a voltage adjuster 31, and an input level converter 32 is applied to an input 33 of a phase comparator 23 as an input signal having an appropriate input level. A power supply $V_{DD}$ 36 provides a power to the active elements of the voltage adjuster 31 and converter 32. The oscillation voltage detector 22 provides a stabilized feedback signal irrespective of the state of the loads on the handpiece 12 or 13. The output signal from the oscillation voltage detector 22 is delivered to the phase comparator 23 of a PLL 28 where the feedback signal is compared with a reference signal of substantially the same frequency as the resonant frequency generated by a voltage controlled oscillator (VCO) 26 with reference to phase, and the phase difference is integrated into a saw-tooth wave by a low pass filter 24 like a lag filter of capacitors and resistors. The resulting saw-tooth signal is amplified by a differential amplifier 25 the output from which is inputted to the VCO 26. The feedback signal 27 substantially locked by a control voltage from the VCO 26 is fed back to the amplifier 5 and then to the PLL 28 again via the filter 6, transformer 7, amplifier 8, transformer 9, matching circuit 10 and oscillation voltage detector 22. This operation is repeated to bring about a locked state or a resonant frequency state. Thus, even if the operation section at the end of the ultrasonic vibration transmitter of the handpiece 12 or 13 has a load thereon from prior to vibration thereof, namely, even if the resonant frequency is very difficult to generate, access to an optimum resonant frequency or locked state is repeated and finally an ultrasonic operation at the resonant frequency is brought about. Therefore, even if the operation section is embedded either in a large-load hard organization or in a soft calcified organization, a vibration of a stabilized amplitude is easily obtained. The phase comparator 23, low pass filter 24 and differential amplifier 25 are preferably those shown in FIG. 4, although not especially limited. The VCO 26 is preferably made of crystal, LC, CR or ceramics, although not especially limited.

Figure 5:
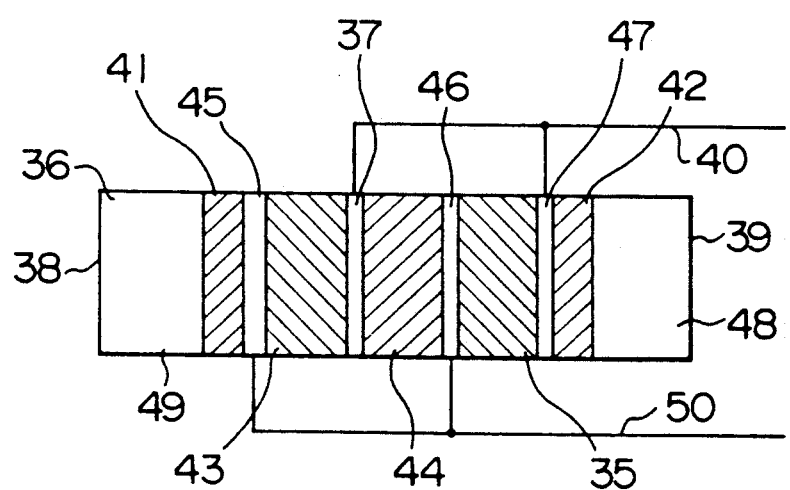
FIG. 5 illustrates the structure of a bolted CF-type Langevin transducer.

FIG. 5 shows a bolted Langevin type transducer as one embodiment of the present invention. The transducer 36 includes ring-like electrostrictive elements, 43, 44, 35 ring-like electrodes 45, 37, 46, 47 alternating with the electrostrictive elements, insulator ceramic rings 41 and 42 outside the end electrodes 45 and 47, a metal block 49 having a bolt portion which extends through the ceramic rings 41, 42 electrostrictive elements 43, 44, 35 and electrodes 45, 37, 46, 47 and a metal block nut 48 which cooperates with the bolted metal block 49 to tighten the elements therebetween. By supplying a current of a predetermined high frequency to leads 40 and 50 to the respective electrodes, ultrasonic vibrations occur at the ends 38 and 39 of the transducer 36.

In the present invention, any electrostrictive device may be used if it can withstand the tightening pressure. The preferable material is PZT (plumbous zirconate titanate). The insulator ceramics used may be ones of electrical resistance of more than $10^{13}$ $\Omega$cm and of less than a dielectric constant of 20, for example, $Al_2O_3$ or $ZrO_2$ ceramics, but not limited to them. The materials of the metal blocks used may be stainless steel, titanium alloy, aluminum alloy, etc., but not limited to them.

While the direction and amplitude of vibrations of the transducer are not especially limited, it is desirable to design the overall length of the transducer so as to be an integral times one half of the resonating vibration wavelength to obtain high energy efficiency. Provision of a fluid path in the transducer 36 serves to cool the transducer.

Figure 6:
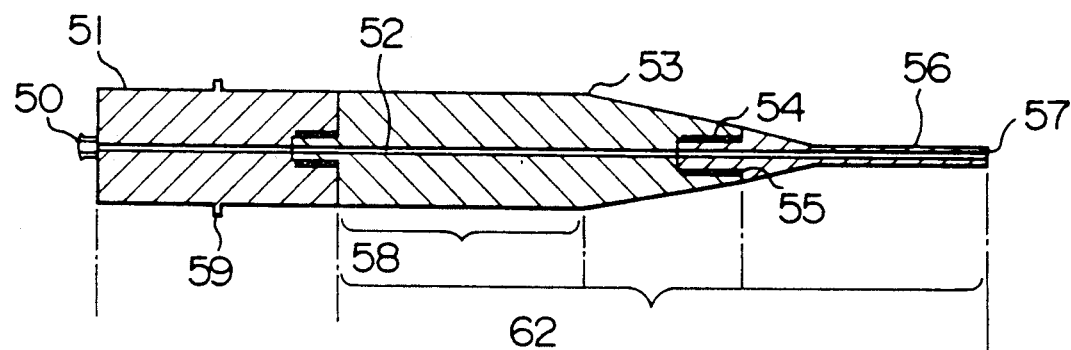

FIG. 6 illustrates a handpiece as one example of the present invention. It includes an ultrasonic vibration source 51 and a vibration transmitter 62 engaged threadedly with the source. The vibration transmitter 62 include a connection portion 53 and an operation section 56 engaged threadedly with the connection portion. A fluid path 52 extends longitudinally through the ultrasonic vibration source 51, connection portion 53 and operation section 56 at the outer end 57 of which the amplitude of vibrations appears as a side 61 shown in FIG. 8. The amplitude of the mechanical vibrations of an ultrasonic frequency generated by the ultrasonic vibration source 51 is amplified by a change in the cross section area of the connection portion 53 and operation section 56, the resulting vibration is transmitted to the operation end 57 to crush part of the organization of an organism and the fragments of the crushed organization are sucked and discharged via the fluid path 52.

Figure 7:
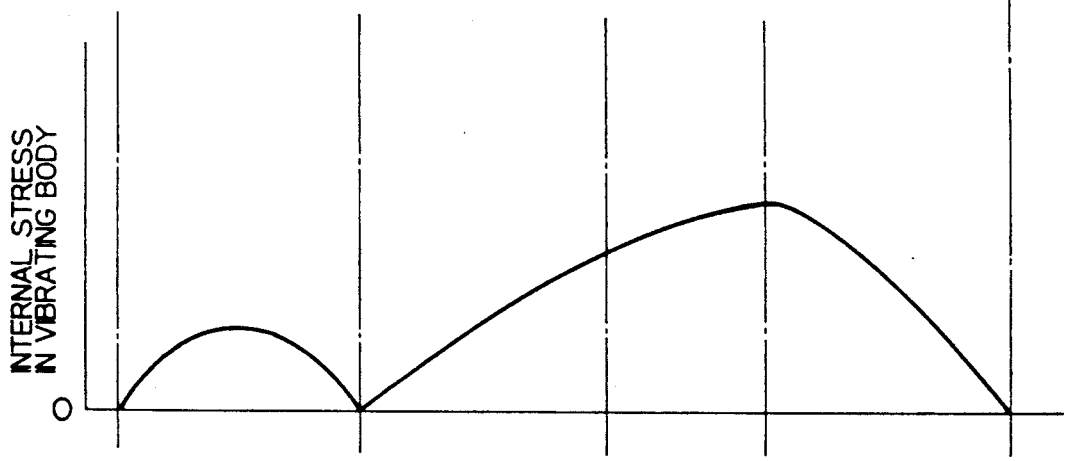
Figure 8:
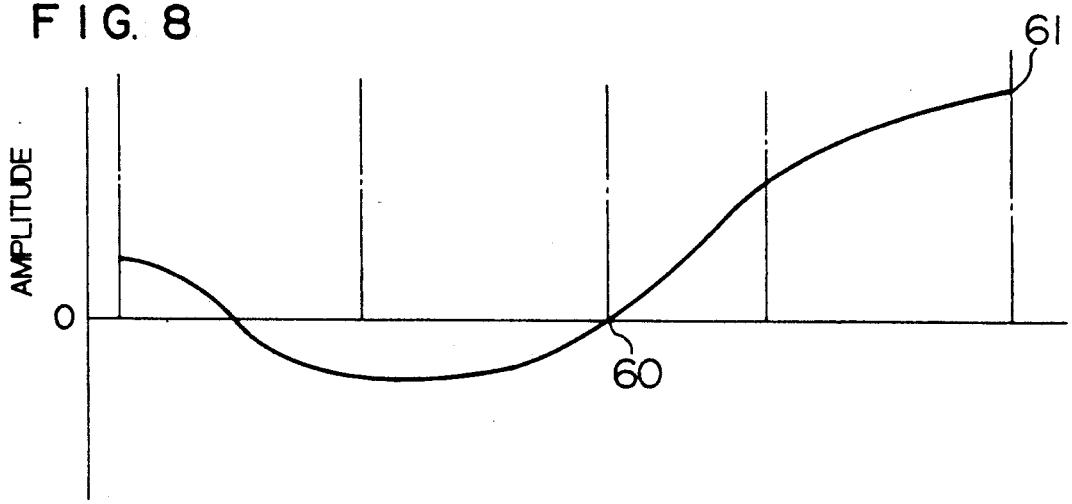
Figure 21:
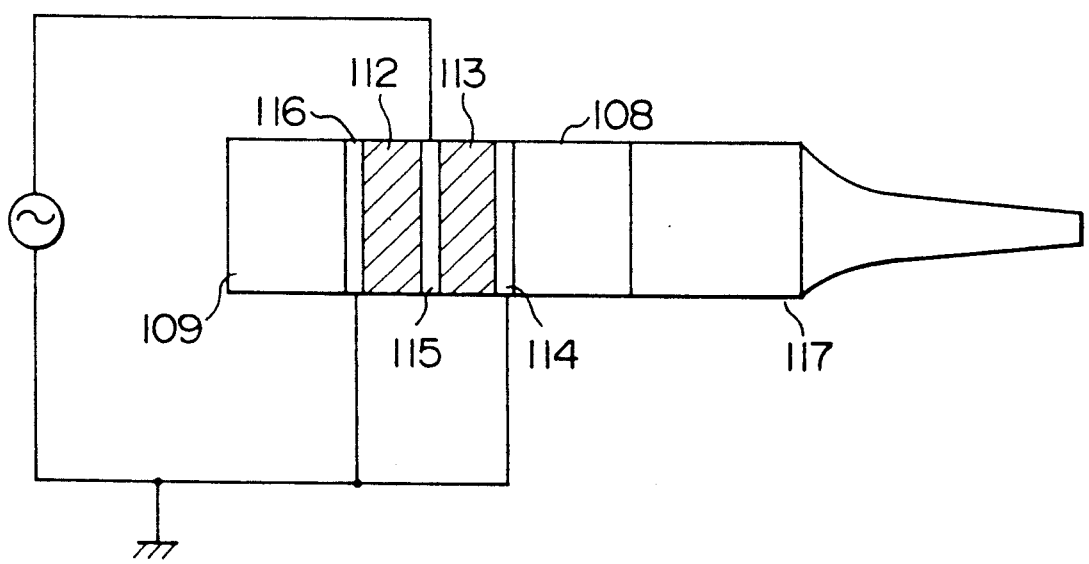
FIGS. 21 and 22 illustrate the shape, and amplitude, distribution of stress of the conventional ultrasonic vibration transmitter.
Figure 22:
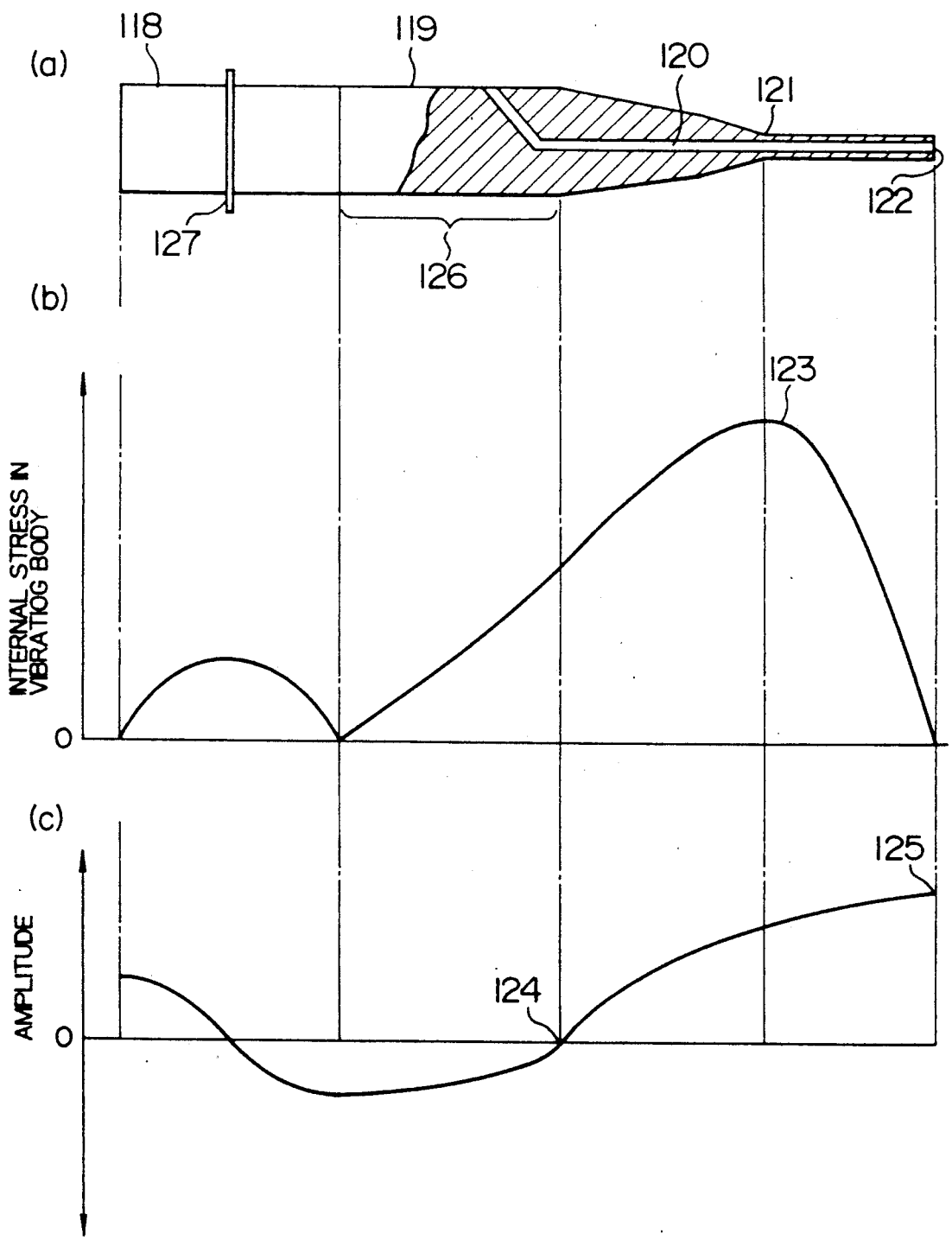

The connection portion 53 has a constant cross-sectional area (cylindrical stem) portion 58 extending from the adjacent end of the ultrasonic vibration source 51 to a position where a node of vibration 60 shown in FIG. 8 is formed and a tapering portion integral with the cylindrical portion engaged threadedly at 54 with a tapering base of the operation section 56 so as to form a merged tapering section. Therefore, as shown in FIG. 7, the maximum stress is produced at a position close to the contact face 55 of larger cross section area than the conventional handpiece (see FIGS. 21 and 22) and reduced by 20-50% even if the outer shape of the vibration transmitter 62 is the same as the conventional one. The threads are preferably fine, but the pitch itself is influenced by the size of the threads and not especially limited. In addition to threaded engagement, welding or pinning may be employed. The position of the contact face 55 where the operation section 56 and connection portion 53 are connected is determined by the material of the connection portion 53 in a position from the node 60 of vibration in the connection portion 53. The length of the tapering portion of the connection portion 53 is preferably $\frac{1}{8}$-1/10 of the wavelength of vibration.

By employing the density of the connection portion 53 material higher than that of the operation section 56, the amplitude amplification rate increases in direct proportion to the ratio in density of the connection portion material to the operation section 56 material to thereby provide a larger amplitude than the conventional one even if the stresses produced at the operation section 56 and connection portion 53 are the same as those in the conventional operation section and connection portion. For example, if the connection portion 53 and operation section 56 are made of stainless steel and titanium alloy, respectively, the ratio in density of the stainless steel and titanium alloy is 9:5 and appears as an increase of 180% in the amplitude amplification rate and the amplitude increases by 180% even if the connection portion and operation section is the same in shape as the conventional one.

Figure 9:
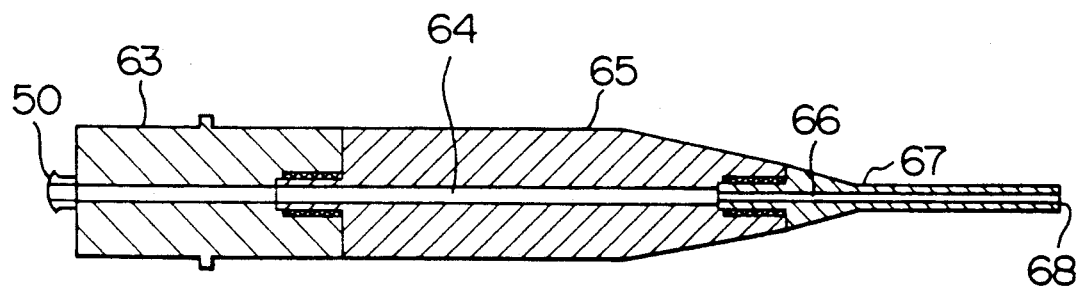

FIG. 9 illustrates an embodiment of the invention in which the fluid path 64 extending through the ultrasonic vibration source 63 and connection portion 65 is larger in cross section area than the fluid path 66 in the operation section 67. Therefore, the size of fragments of the organism organization crushed by the operation end 68 is smaller than the cross sectional area of the fluid path 64, so that even when the fragments pass through the fluid path 64 smaller in amplitude than the operation end 68, they easily pass through the fluid path 64 by vacuum suction to thereby prevent the clogging of the fluid path. The cross-sectional area of the fluid path 64 is preferably 1.3-2.3 times that of the fluid path 66, but not limited.

Figure 10:
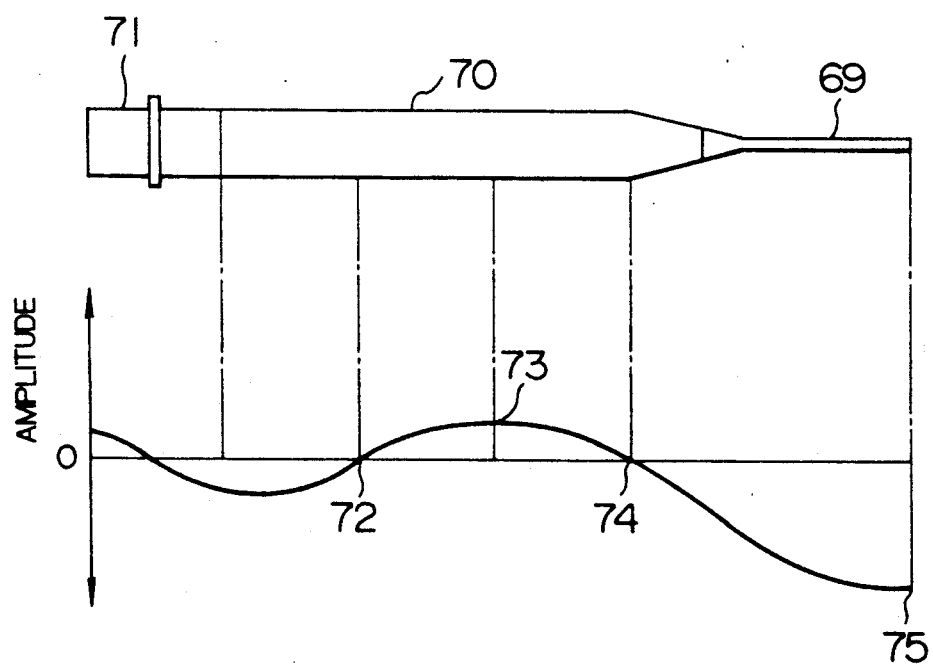
Figure 11:
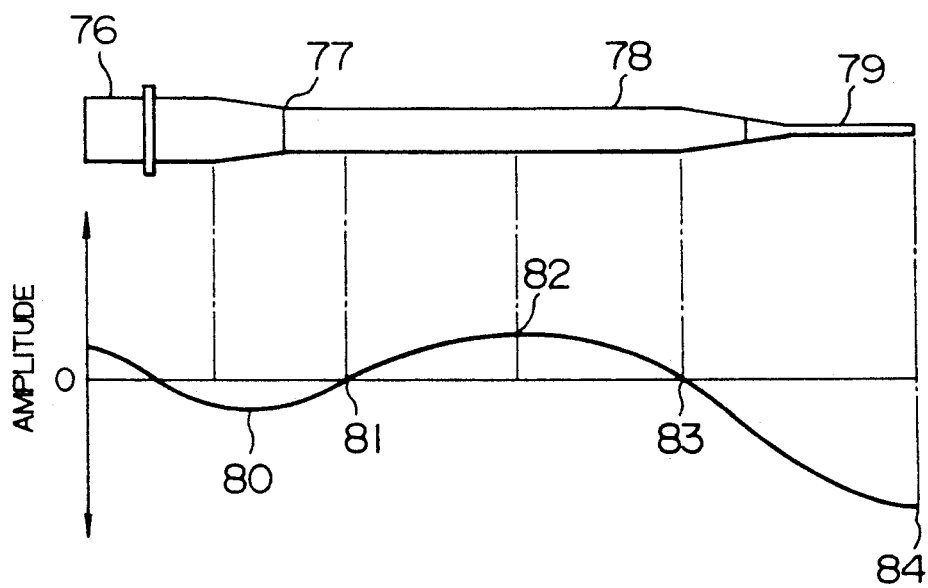
Figure 12:
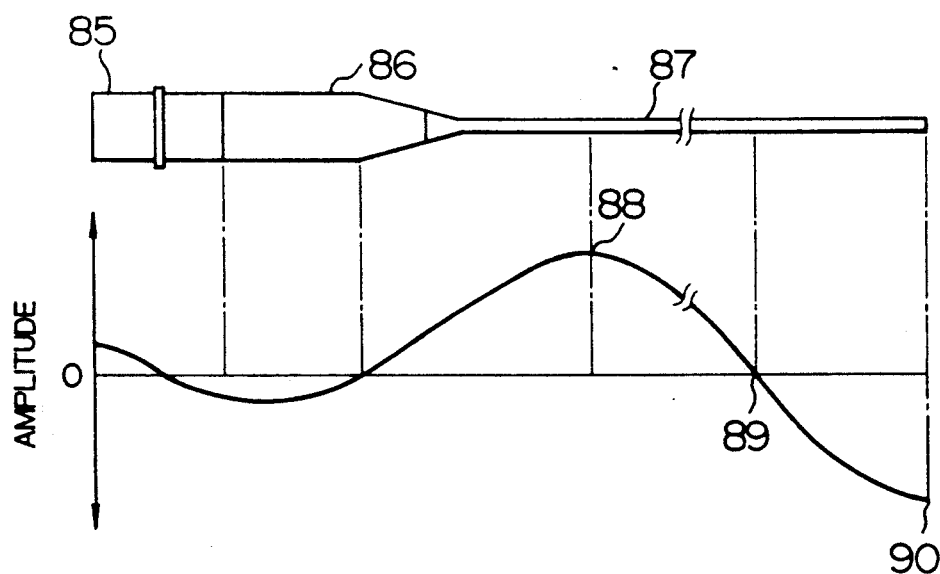
Figure 13:
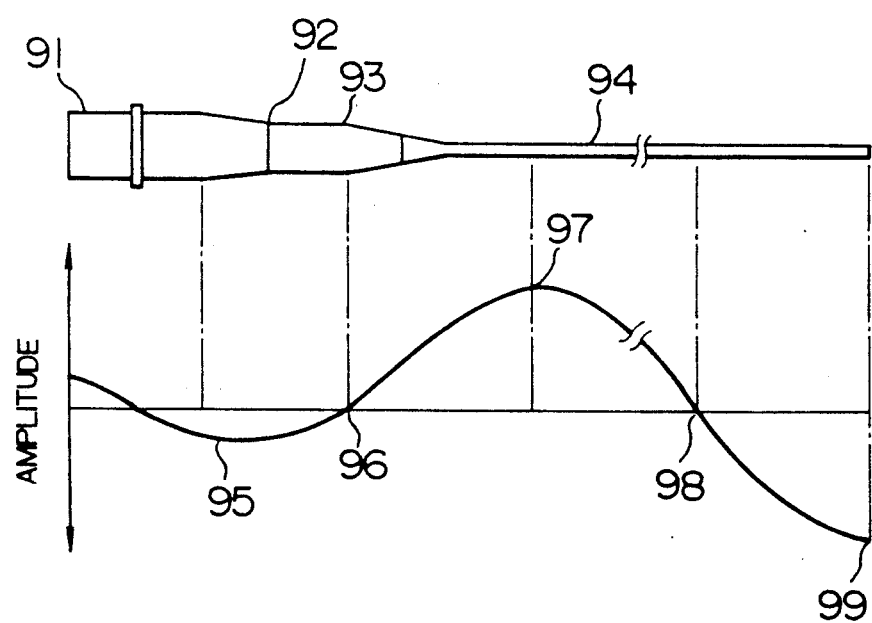

FIG. 10 illustrates an embodiment having a plurality of vibrating nodes 72 and 74. FIG. 11 shows an embodiment in which the junction 77 between the ultrasonic vibration source 76 and connection portion 78 is between the sides of vibrations 80 and 81. FIG. 12 shows an embodiment in which the operation section 87 has a plurality of vibration sides 88 and nodes 89. FIG. 13 shows an embodiment in which the operation section 94 has a plurality of sides 97 and nodes 98 and in which the ultrasonic vibrations source 91 is connected to the connection portion 93 between a node 96 and a side 95 of vibration. The embodiments of FIGS. 10-13 are each a handpiece which reduces the stress and increases the amplification rate, is excellent in durability and provides a large amplitude.

FIG. 14A illustrates an embodiment in which the connection portion 53 is bent with reference to the longitudinal axis. FIG. 14B illustrates an embodiment in which the operation section 56 is bent at an angle of 5-120 degrees to the longitudinal axis of the connection portion.

FIG. 15A illustrates a vibration transmitter 210 to cut a hard organization. An irrigation liquid is led from an inlet 213 through an irrigation path 212 to an outlet 214 and ejected therefrom against the operation end 211, the organization of an organism portion to be cut, and its neighborhood. The irrigation liquid prevents the generation of frictional heat in the portion to be cut and in the vibration transmitter 210 and hence the deterioration of the vibration transmitter. As shown in FIG. 15B, the use of a rugged wedge-like blade 215 formed on the operation section serves to start vibrations easily even if it is sticked into a hard organization, and the cutting efficiency is doubled compared to a regular wedge-like blade. Although the dimensions of the rugged shape of the blade is not specially limited, the thickness of the blade is preferably 1.0-2.5 mm and the crest-crest or valley-valley pitch is preferably 1-5 mm. The number of crests or valleys in the blade is preferably 3-10 depending on the size of the operation section 211. While the material of the vibration transmitter 210 is not particularly limited, it is preferably titanium alloy. The operation section 211 may be a removable one of titanium alloy or ceramic.

Figure 16A:
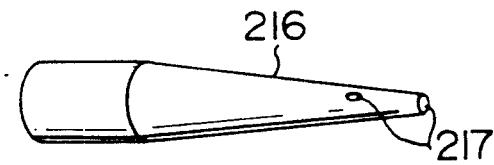
Figure 16B:
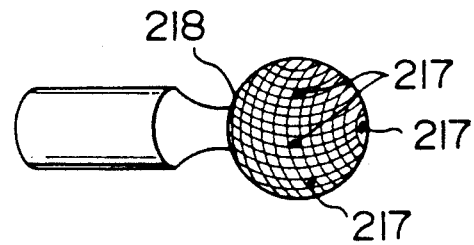
Figure 16C:
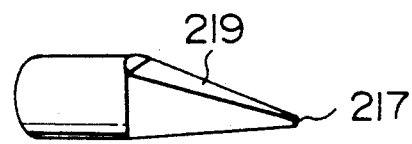
Figure 16D:
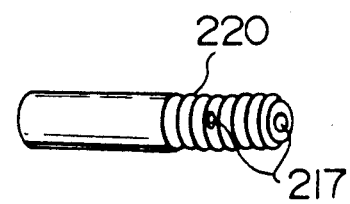
Figure 16E:
Figure 16F:
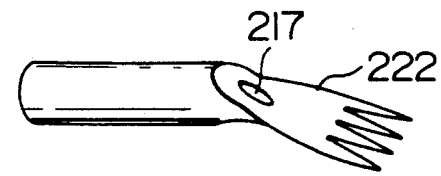
Figure 16G:
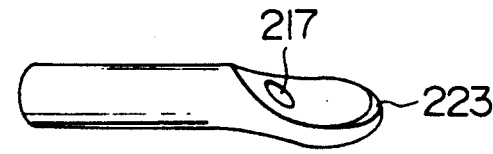

FIGS. 16A-16H illustrate embodiments of the operation section for severing and cutting purposes. FIG. 16A illustrates a conical operation section 216. FIG. 16B illustrates a ball-like operation section 218. FIG. 16C illustrates a prismatic operation section 219. FIG. 16D illustrates a ring-like operation section 220. FIG. 16E illustrates a scoop-like operation section 221. FIG. 16F illustrates a fork-like operation section 222. FIG. 16G illustrates a spoon-like operation section 223. Each operation section has an outlet 217 for an irrigation liquid, so that the generation of heat in the operation section and thermal damage to the organization around the operation section are prevented. The operation sections produced from a hard organization by serving and cutting are washed away to ensure the field of view of operation is ensured. While the material of the operation section is not especially limited, stainless steel, titanium alloy or ceramics are preferable. The number of outlets 217 is not especially limited. The operation section may be of a removable type.

Figure 16H:
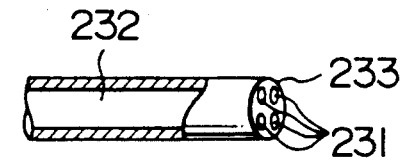

FIG. 16H illustrates an embodiment in which the operation section 233 has a plurality of openings 231 for the suction path 232 to cut a mass of calcium depositing on a soft organization and to suck calcium fragments away. Provision of the plurality of openings 231 serves to suck small fragments of calcium to thereby prevent clogging of the suction path.

Figure 17A:
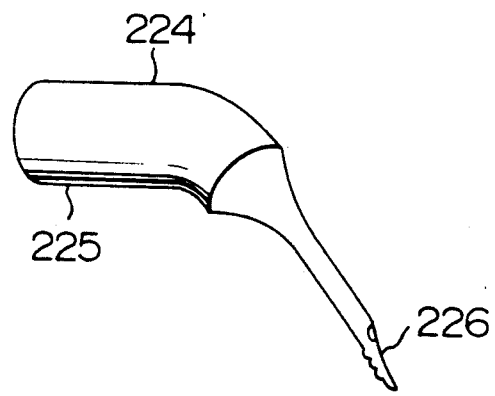
Figure 17B:
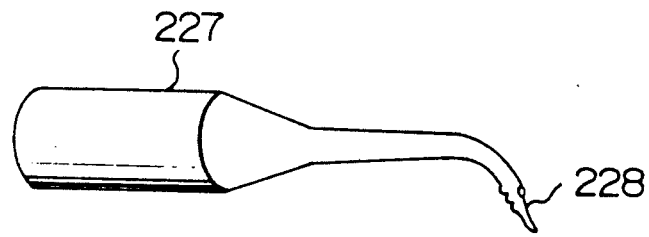

FIG. 17A illustrates an embodiment in which the operation section 226 is of a blade type, and the connection portion 225 of the vibration transmitter 224 is bent relative to the longitudinal axis of the handpiece. The bend angle is not especially limited, but is preferably 5-45 degrees. FIG. 17B illustrates one example of a bent blade-like operation section 228 of the vibration transmitter 227. The bent angle is not limited, but is preferably 5-30 degrees.

Figure 18:
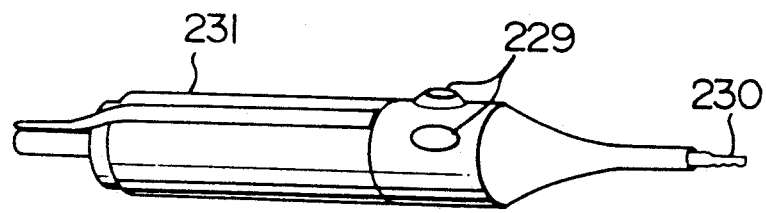
FIG. 18 illustrates the shape of a handpiece with a switch.
Figure 19:
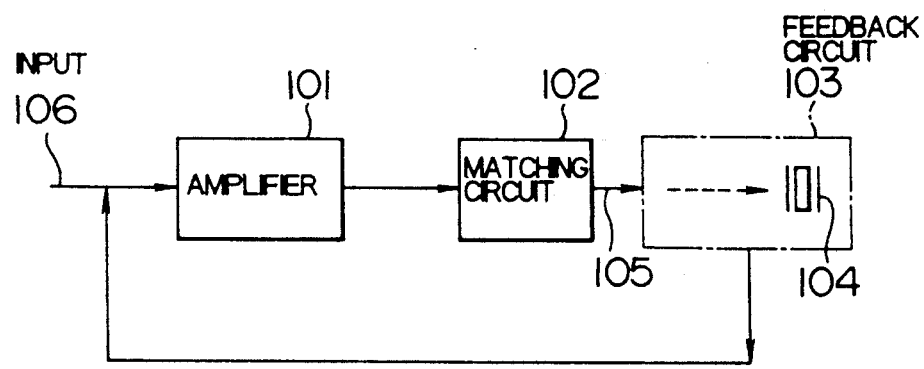
FIGS. 19 and 20 are a block diagram and a circuit diagram, respectively, of a conventional oscillator.
Figure 20:
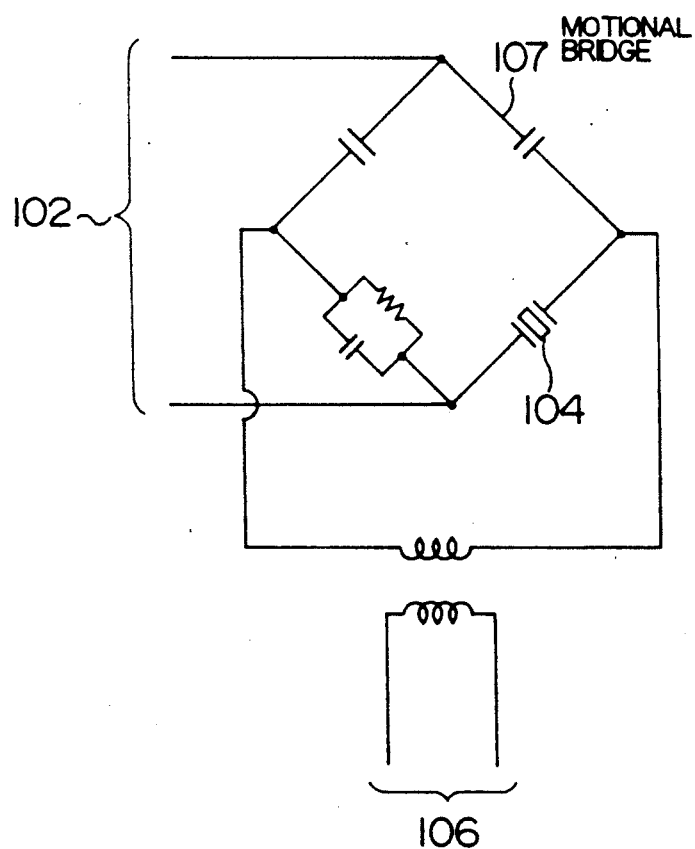

FIG. 18 illustrates an embodiment in which switches 229 are provided on a handpiece 231 to turn on and off ultrasonic vibrations. The switch 229 is a waterproof momentary touch switch giving a clicking sensation and preferably made of a fluororubber, and the surface diameter of the switch 229 is preferably 5-15 mm, but not especially limited. The material of the handpiece 231 is preferably a plastic material such as heat-resisting polysulfone, polyamide, polyimide, polyamidoimide, PTFE, ETFE, epoxy or phenol resin or a metal such as an aluminum alloy, titanium alloy or stainless steel alloy. It preferably has a heat resistance higher than 130° C.

According to the present invention, the mechanical resonant frequency can be traced over a wide range in correspondence to fluctuations of a load during vibration. The vibration starts at an appropriate mechanical resonant frequency irrespective of the state of the loads on the handpieces at the start-up whereas the conventional ultrasonic oscillator can only start to oscillate when it has no load or substantially no load (for example, when the surgery device is placed in water). According to the inventive device, the handpiece includes a CF type transducer the leakage current of which is very small, for example, less than 10 μA compared to a conventional bolted Langevin type transducer, so that the device is also usable in heart operation. The ultrasonic vibration transmitter in the present invention has a composite structure of the connection portion and operation section excellent in durability compared to the conventional transmitter. Severing/cutting a hard organization can be effected without damaging its ambient organization thermally, while it is difficult for the conventional surgical bur to do so. Provision of touch switches on the handpieces facilitates the manipulation by the operator and contributes advantageously to microsurgery which requires fine manipulation. As just mentioned above, the surgical operation device according to the present invention is suitable for crushing and removing soft organizations and a calcium mass and a calcified organization in the field of brain surgery, heart surgery, digestive surgery or severing and cutting a hard organization in the field of oral surgery, orthopedic surgery, plastic surgery, etc.

We claim:

1. A surgical operation device comprising:
   an ultrasonic piezoelectric transducer means for generating ultrasonic vibrations;
   an oscillation feedback type oscillator means for supplying high-frequency power to the piezoelectric transducer means;
   an ultrasonic vibration transmitter means connected to the piezoelectric transducer means for transmitting and amplifying the ultrasonic vibrations generated by the piezoelectric transducer means;
   a sucking unit; and
   an irrigator;
   wherein the piezoelectric transducer means includes a bolted Langevin type transducer;
   wherein the oscillation feedback type oscillator means comprises a feedback circuit which includes a PLL and an oscillation voltage detector engaged to an input of said PLL for generating a feedback oscillation signal for input into the oscillation voltage detector, said PLL including a phase comparator, a low pass filter, a differential amplifier, and a voltage controlled oscillator connected in series to produce the feedback oscillation signal, and wherein said oscillation voltage detector includes a motional bridge, a base clipper, a voltage adjuster and an input level converter connected in series for input into said PLL, wherein said motional bridge has a branch including said Langevin type transducer driven by the feedback oscillation signal and a second branch including capacitors.

2. A surgical operation device according to claim 1, wherein the Langevin type transducer includes a stack of alternating ring-like electrorestrictive elements and ring-like electrodes one larger in number than the electrostrictive elements and connected electrically in parallel, a pair of insulators holding the stack therebetween, a pair of metal blocks placed outside the corresponding insulators and a bolt tightening said electrostrictive elements by extending through the center of said electrostrictive elements.

3. A surgical operation device according to claim 2 wherein the insulators each include a ceramic material having an electrical resistance higher than $10^{13}$ Ωcm.

4. A surgical device according to claim 1, wherein the ultrasonic vibration transmitter means includes a connection portion which comprises a stem portion of a constant cross-sectional area and a tapering portion extending from the stem portion, an operation section, and means for removably connecting the operation section to the tapering portion wherein a maximum point of internal stress produced by the ultrasonic vibrations occurs at a junction between the stem portion and the tapering portion and a maximum amplitude of the ultrasonic vibrations occurs at a free end of the operation section.

5. A surgical operation device according to claim 4, wherein said means for removably connecting the tapering portion and said operation section includes a screw thread.

6. A surgical operation device according to claim 4, wherein the connection portion and the operation section each have a fluid path extending therethrough.

7. A surgical, operation device according to claim 6, wherein a cross sectional area of the fluid path in the connection portion is equal to, or larger than, that of the fluid path in the operation section.

8. A surgical operation device according to claim 4, wherein a density of the material of the connection portion is equal to, or higher than, a density of the material of the operation section.

9. A surgical operation device according to claim 4, wherein a forward portion of the operation section is bent at an angle in the range from 5 to 120 degrees to the longitudinal axis of the connection portion.

10. A surgical operation device according to claim 1, wherein the ultrasonic vibration transmitter means includes an operation section with a blade portion adapted to contact an organism and has a fluid path extending therethrough, one end of the path being open in the operation section.

11. A surgical operation device according to claim 10, wherein the ultrasonic vibration transmitter means includes a connection portion extending in the same direction as the ultrasonic vibrations.

12. A surgical operation device according to claim 10, wherein said operation section includes an end operation portion which extends at an angle to the direction of the ultrasonic vibrations.

13. A surgical operation device according to claim 10, wherein the ultrasonic vibration transmitter means includes a connection portion extending at an angle to the direction of the ultrasonic vibrations.

14. A surgical operation device according to claim 1, including a handpiece and a switch provided on a side of said handpiece, said handpiece including the bolted Langevin type transducer and the ultrasonic vibration transmitter means.

15. A surgical operation device comprising:
an ultrasonic piezoelectric transducer means for generating ultrasonic vibrations;
an oscillation feedback type oscillator means for supplying high-frequency power to the piezoelectric transducer means;
an ultrasonic vibration transmitter means connected to the piezoelectric transducer means for transmitting and amplifying the ultrasonic vibrations generated by the piezoelectric transducer means;
wherein the piezoelectric transducer means includes a bolted Langevin type transducer;
wherein the oscillation feedback type oscillator means includes a feedback circuit which comprises means for widely tracing the ultrasonic vibrations in accordance with load fluctuation and
wherein said means for widely tracing includes an oscillation voltage detector, a motional bridge, a base clipper, a voltage adjuster and an input level converter, said motional bridge having a first branch including said Langevin type transducer and a second branch including capacitors.

16. A surgical operation device comprising:
an ultrasonic piezoelectric transducer means for generating ultrasonic vibrations;
an oscillation feedback type oscillator means for supplying high-frequency power to the piezoelectric transducer means;
a vibration transmitter means connected to the piezoelectric transducer means for tnramsitting and amplifying the ultrasonic vibrations generated by the piezoelectric transducer means;
wherein the piezoelectric transducer includes a bolted Langevin type transducer;
wherein the oscillation feedback type oscillator means includes a feedback circuit which comprises means for providing a stabilized feedback signal irrespective of a state of a load on said piezoelectric transducer means and
wherein said means for providing a stabilized feedback signal includes an oscillation voltage detector, a motional bridge, a base clipper, a voltage adjuster and an input level converter, said motional bridge having a first branch including said Langevin type transducer driven by the stabilized feedback signal and a second branch including capacitors.

* * * * *